(12) United States Patent
Naylor

(10) Patent No.: US 9,895,535 B2
(45) Date of Patent: Feb. 20, 2018

(54) HEARING ASSISTANCE SYSTEM WITH IMPROVED SIGNAL PROCESSING COMPRISING AN IMPLANTED PART

(71) Applicant: Oticon A/S, Smørum (DK)

(72) Inventor: Graham Naylor, Smørum (DK)

(73) Assignee: Oticon A/S, Smørum (DK)

( * ) Notice: Subject to any disclaimer, the term of this patent is extended or adjusted under 35 U.S.C. 154(b) by 0 days.

(21) Appl. No.: 14/820,114

(22) Filed: Aug. 6, 2015

(65) Prior Publication Data
US 2016/0038738 A1    Feb. 11, 2016

(30) Foreign Application Priority Data
Aug. 7, 2014   (EP) .................................... 14180154

(51) Int. Cl.
*A61N 1/36*   (2006.01)
*A61B 5/04*   (2006.01)
(Continued)

(52) U.S. Cl.
CPC ...... *A61N 1/36032* (2013.01); *A61B 5/04001* (2013.01); *A61B 5/125* (2013.01);
(Continued)

(58) Field of Classification Search
None
See application file for complete search history.

(56) References Cited

U.S. PATENT DOCUMENTS

| | | |
|---|---|---|
| 5,758,651 A | 6/1998 | Nygard et al. |
| 2006/0013858 A1* | 1/2006 | Trune ................ A61K 31/573 424/427 |

(Continued)

FOREIGN PATENT DOCUMENTS

| | | |
|---|---|---|
| EP | 2200347 A2 | 9/2013 |
| WO | WO 2013/142843 A1 | 9/2013 |

OTHER PUBLICATIONS

Mercier et al. "Energy extraction from the biologic battery in the inner ear", nature biotechnology letters, published online Nov. 8, 2012, pp. 1-5.
(Continued)

*Primary Examiner* — Ankit D Tejani
(74) *Attorney, Agent, or Firm* — Birch, Stewart, Kolasch & Birch, LLP

(57) ABSTRACT

The application relates to a hearing assistance system (a method and its use) for processing an input signal representative of sound according to a user's needs, the hearing assistance system comprising an implanted part adapted for being at least partially implanted in a user's head and comprising a sensing unit capable of measuring an endocochlear potential at one or more positions along the length of the cochlear partition. The hearing assistance system further comprises a decoder configured to receive said endocochlear potentials or signals derived therefrom and to transform the received signals into signals appropriately conditioned for use as control inputs to the signal processing unit, and wherein the signal processing unit is configured to process the electric input signal in dependence of said control inputs from said decoder. Thereby the processing of the audio signal of a hearing assistance device can be automatically adapted over time.

19 Claims, 9 Drawing Sheets

(51) Int. Cl.
*A61B 5/12* (2006.01)
*A61B 5/00* (2006.01)
*A61N 1/05* (2006.01)
*A61N 1/372* (2006.01)
*H04R 25/00* (2006.01)

(52) U.S. Cl.
CPC .......... *A61B 5/6817* (2013.01); *A61N 1/0541* (2013.01); *H04R 25/70* (2013.01); *A61B 2560/0204* (2013.01); *A61N 1/37211* (2013.01); *H04R 25/552* (2013.01); *H04R 2225/55* (2013.01); *H04R 2225/67* (2013.01)

(56) References Cited

U.S. PATENT DOCUMENTS

| | | | | |
|---|---|---|---|---|
| 2007/0078177 | A1* | 4/2007 | Bao | A61K 31/4015 514/425 |
| 2008/0221640 | A1 | 9/2008 | Overstreet et al. | |
| 2012/0059435 | A1* | 3/2012 | Daly | A61N 1/08 607/57 |
| 2012/0245666 | A1* | 9/2012 | Jolly | A61N 1/36032 607/137 |
| 2012/0300964 | A1* | 11/2012 | Ku | A61B 5/04845 381/321 |
| 2012/0302859 | A1* | 11/2012 | Keefe | A61B 5/121 600/383 |
| 2013/0343584 | A1* | 12/2013 | Bennett | H04R 25/554 381/315 |

OTHER PUBLICATIONS

Richard A. Schmiedt "The Physiology of Cochlear Presbycusis", Chapter 2, pp. 9-38, in S. Gordon-Salant et al. (eds.),The Aging Auditory System, Springer Handbook of Auditory Research 34, DOI 10.1007/978-1-4419-0993-0_2, Springer Science + Business Media, LLC, 2010.

* cited by examiner form a hearing assistance system in accordance with the present disclosure.

HEARING ASSISTANCE SYSTEM WITH IMPROVED SIGNAL PROCESSING COMPRISING AN IMPLANTED PART

TECHNICAL FIELD

The present application relates to a hearing assistance system for enhancing a sound signal according to a particular user's needs. The disclosure relates specifically to a hearing assistance system comprising an implanted part adapted for being at least partially implanted in a user's head and to its use. In particular, the hearing assistance system comprises a sensing unit capable of sensing the endocochlear potential (EP) at one or more positions along the length of the cochlear partition.

The application furthermore relates to a method of operating a hearing assistance system.

The application further relates to a data processing system comprising a processor and program code means for causing the processor to perform at least some of the steps of the method.

Embodiments of the disclosure may e.g. be useful in applications such as hearing assistance devices for automatically adapting device features, e.g. processing algorithms, over time.

BACKGROUND

The following account of the prior art relates to one of the areas of application of the present application, hearing aids.

Hearing assistance devices (acoustic or bone-anchored hearing aid, implant, headset, telephone etc.) manipulate their input signals in deliberate ways before presenting them to the ear. In some applications this manipulation includes aspects (e.g. gain, frequency response, compression, noise reduction) intended to compensate for a deviation from normal function in the cochlea of the user. At present, the user's cochlear function is grossly estimated on the basis of either assumed average function (in the case of applications for supposedly normal-hearing listeners) or diagnostic indicators (in the case of hearing-impaired listeners). In both cases, it is assumed that the user's cochlear function is stable over time. Furthermore, any diagnostic indicators (e.g. hearing thresholds) are at best only indirectly correlated with the physiological status of the cochlea. Thus the signal manipulation taking place in the hearing device cannot truly take account of the current functional status of the cochlea which is receiving and transducing those signals for the user to hear. This limits the user benefits which can be obtained.

[Mercier et al, 2012] deal with the topic of energy extraction from electrochemical processes in the inner ear. It is proposed to use the Endocochlear potential (EP) generated in the inner ear as a power source for electronic devices, e.g. to power chemical and molecular sensors, or drug-delivery actuators for diagnosis and therapy of hearing loss and other disorders.

US2012300964A1 describes a method of testing a hearing ability of a user. A hearing aid is adapted to output a sound to test a hearing ability of a user, to detect an electrical signal generated in a body of the user as a result of the output sound, to amplify the electrical signal detected by an electrode unit, and to determine an amplification ratio of a surrounding sound detected by the hearing aid based on characteristics of peaks of waveforms of the amplified signal.

EP2200347A2 deals with a method of operating a hearing instrument based on an estimation of present cognitive load of a user, e.g. by measuring an ambulatory electroencephalogram (EEG), e.g. using suitable electrodes in the surface of a hearing aid shell where it contacts the skin inside or outside the ear canal.

SUMMARY

The mammalian cochlea possesses structures and electrochemical processes, which comprise a 'biologic battery' providing an electrical potential, the endocochlear potential (EP). The EP provides power for the transduction processes which are essential for hearing. The EP is maintained ('recharged') by metabolic processes in the cochlea. With age, the processes maintaining EP deteriorate, affecting hearing. Other things currently known or implicated in degraded or fluctuating EP include noise exposure, smoking and Menieres disease.

It has recently been demonstrated that the EP may be monitored in vivo, and furthermore that energy may be harvested from the EP to power a miniature wireless transmitter [Mercier et al, 2012].

The present disclosure provides a hearing assistance system comprising:
  A sensing unit capable of sensing the endocochlear potential at one or more positions along the length of the cochlear partition, and configured to broadcast this data (e.g. periodically, e.g. using wireless transmission),
  A hearing assistance device comprising
    A (possibly wireless) receiver configured to receive the data from the sensing unit,
    A decoder, configured to transform the received signals into signals appropriately conditioned for use as control variables in the hearing assistance device,
    A signal processing unit configured to perform calculations integrating the cochlear status signals into the overall calculation scheme of the hearing device, such that the manipulations of the input signals of the hearing assistance device may be modified in dependence thereof.

The disclosed hearing assistance system represents an improvement over previously known solutions because
1. It enables the signal processing in a hearing device to be better tailored to the individual and time-varying function of the user's ear,
2. It enables continuous monitoring of cochlear function and triggering of advisory messages.

It has been shown that a degradation of the endocochlear potential is an indicator of or leads to a hearing loss (decreased sensitivity, larger hearing threshold) which in its frequency dependence resembles a typical age related hearing loss (presbyacusis hearing loss).

The present disclosure proposes to use a measurement of the endocochlear potential at a given point in time to indicate an 'effective age' (or an 'effective state or load') of cochlea. By correlating such present 'effective age' or 'effective state' with average hearing loss data (e.g. stored in a hearing aid), processing parameters can be optimized using a (e.g. onboard) fitting algorithm. Thereby important parameters such as frequency dependent gain, compression, etc. can be adapted to the present state of the user's ear. Other processing algorithms such as directionality, noise reduction, etc. may likewise be adapted over time in dependence of the present (measured) endocochlear potential.

An object of the present application is to enable a modification of a hearing assistance system according to the present condition of a user's auditory system, in particular to the present state of a user's cochlea.

Objects of the application are achieved by the invention described in the accompanying claims and as described in the following.

A Hearing Assistance Device:

In an aspect of the present application, an object of the application is achieved by a hearing assistance system for processing an input signal representative of sound according to a user's needs. The hearing assistance system comprises an input unit for receiving said input signal and providing an electric input signal, a signal processing unit for processing said electric input signal according to a set of processing parameters and providing a processed output signal, the signal processing unit having one or more control inputs for influencing said processing parameters. The hearing assistance system further comprises an implanted part adapted for being at least partially implanted in a user's head. The implanted part comprises a sensing unit capable of measuring an endocochlear potential at one or more positions along the length of the cochlear partition. The hearing assistance system further comprises a decoder, configured to receive said endocochlear potentials or signals derived therefrom and to transform the received signals into signals appropriately conditioned for use as control inputs to the signal processing unit. The signal processing unit is further configured to process the electric input signal in dependence of the control inputs from said decoder.

An advantage of the system is that the processing of an audio signal in a hearing assistance system can be automatically adapted over time.

In an embodiment, the implanted part comprises a transmission unit for transmitting said endocochlear potential or a signal, e.g. a voltage difference, based thereon (e.g. to another part of the hearing assistance system and/or to another device). In an embodiment, the transmission unit comprises an antenna and a wireless transceiver, e.g. for establishing a link to an external (non-implanted) part of the hearing assistance system. In an embodiment, the transmission unit is based on near-field (e.g. capacitive or inductive) coupling to a corresponding external reception unit. Alternatively, the transmission unit is based on far-field electromagnetic communication.

In an embodiment, the implanted part is configured to measure (or record (e.g. store), and possibly transmit) said endocochlear potential according to a predefined criterion, e.g. at different points in time $t_n$, where $t_n$ are discrete values of time (n is a time index), e.g. at predefined points in time, or if a value of the endocochlear potential have changed more than a predefined relative or absolute amount, and/or if a rate of change (over time) of an endocochlear potential is above a predefined size. In an embodiment, said predefined criterion comprises measuring the endocochlear potential periodically over time, e.g. with a predefined (or adaptively determined frequency).

In an embodiment, the hearing assistance system comprises an alarm unit configured to issue an alarm indication (e.g. an information signal) to the user according to a predefined criterion, e.g. at predefined times, and/or when parameters are changed due to changes in the endocochlear potentials, e.g. if an endocochlear potential changes more than a predefined relative or absolute amount, and/or if a rate of change of an endocochlear potential (over time and/or distance in cochlea) is above a predefined size.

In an embodiment, the hearing assistance system is configured to estimate a received accumulated acoustic dose over a time range based on a change of endocochlear potentials over that time range. In an embodiment, the hearing assistance system is configured to issue an alarm indication when a predefined estimated acoustic dose is exceeded.

In an embodiment, the alarm indication unit is adapted to issue an alarm signal, if a hearing threshold (or a rate of change (difference/time ratio)) exceeds a predefined threshold value (indicating that the user's hearing ability has deteriorated, possibly over a relatively short, or alternatively over a relatively long, period of time, and that the user should act to verify the cause of such deterioration and identify a proper remedy).

In an embodiment, the implanted part (e.g. the sensing unit) comprises an electrode, termed an EP-electrode, for picking up said endocochlear potential (EP) at a position along the length of the cochlear partition. In an embodiment, the EP-electrode is in communication with the sensing unit. In an embodiment, the sensing unit is configured to amplify the endocochlear potentials from (picked up by) said (sensing) EP-electrode. The EP-electrode is preferably configured to be located in cochlea, in particular in scala media, preferably in fluid contact with endolymph.

In an embodiment, the implanted part (e.g. the sensing unit) comprises a number $N_{EP}$ of EP-electrodes ($N_{EP} \geq 2$) for picking up said endocochlear potentials at a number of positions along the length of the cochlear partition. The EP-electrodes are configured to be fully or partially located in scala media, preferably in fluid contact with endolymph. In an embodiment, the EP-electrodes are electrically connected to (or form part of) the sensing unit.

In an embodiment, the implanted part (e.g. the sensing unit) comprises a reference electrode. Preferably, the reference electrode is configured to be located in cochlea, e.g. in scala tympani, preferably in fluid contact with perilymph. The reference electrode is e.g. used as a common voltage for different measurements of endocochlear potentials to provide comparable voltage differences $\Delta V_{EP}$, e.g. over time t, $\Delta V_{EP}(t_n)$, where $t_n$ are discrete values of time, n being a time index. The endocochlear voltage differences may either represent endocochlear potentials measured at one EP-electrode at different points in time, or endocochlear potentials measured at different (spatially separate) EP-electrodes at the same or different points in time (or both).

In an embodiment, the hearing assistance system is configured to measure or determine resulting voltage differences $\Delta V_{EP}(x_i)$ for endocochlear potentials $EP(x_i)$ (i=1, 2, ..., $N_L$), where $N_L$ is the number of locations (electrodes) along the cochlear nerve, where endocochlear potentials are measured. In an embodiment, $N_{EP}=N_L$.

In an embodiment, the hearing assistance system is configured to evaluate the current state or condition of cochlea or the cochlear nerve based on the measured endocochlear potentials. In an embodiment, the hearing assistance system is configured to use the measured endocochlear potentials, or signals derived therefrom, e.g. the resulting voltage differences $\Delta V_{EP}(x_i)$ or amplified versions thereof, to evaluate a current state or condition of cochlea or the cochlear nerve and/or changes therein.

In an embodiment, the hearing assistance system is configured to base said evaluation on statistical measures derived from said measured endocochlear potentials over time and/or location. In an embodiment, the hearing assistance system is configured to determine an average value $\mu_{EP}(x_i)$ and/or a variance $\sigma_{EP}(x_i)$ of $EP(x_i)$ over location $x_i$, i=1, 2, ..., $N_L$, at a given point in time ($t_n$). In an embodiment, the hearing assistance system is configured to determine an average value $\mu_{EP}(x_i, t_n)$ and/or a variance $\sigma_{EP}(x_i, t_n)$ of $EP(x_i, t_n)$ over time $t_n$, n=1, 2, ..., $N_T$, where $N_T$ is the number of measurements performed at different points in time) at a given location $x_i$ (such as for all locations $x_i$, i=1, 2, ..., $N_L$).

In an embodiment, the hearing assistance system comprises a database (e.g. a memory) wherein data linking endocochlear potentials to estimated hearing loss (e.g. hearing thresholds) are stored. Alternatively, the hearing assistance system comprises an interface to an external database from which data linking endocochlear potentials to estimated hearing loss (e.g. hearing thresholds) can be retrieved. In an embodiment, the database comprises corresponding data for endocochlear potentials and measured hearing loss for the user (at a number of stimulation frequencies) at one or more points in time. Preferably, such corresponding values of endocochlear potentials and measured hearing losses (e.g. hearing thresholds) for the user are measured during a fitting of the hearing assistance system to the user and subsequently stored in the database accessible to the hearing assistance system.

In an embodiment, the hearing assistance system comprises or has access to a database wherein data linking endocochlear potentials to estimated accumulated acoustic dose are stored. Preferably, such corresponding values of endocochlear potentials and applied accumulated acoustic dose for the user are measured during a fitting of the hearing assistance system to the user and subsequently stored in the database accessible to the hearing assistance system.

The endocochlear potentials of a particular user may be manipulated by appropriate medical treatment (e.g. drug intake) and/or exposure to predefined levels of acoustic dose. In an embodiment, corresponding values of endocochlear potentials (e.g. manipulated) and hearing thresholds for the user are measured during a fitting of the hearing assistance system to the user and subsequently stored in the database accessible to the hearing assistance system. In an embodiment, the hearing assistance system comprises a programmable probe signal generator configured to apply various controllable accumulated acoustic doses over predefined periods of time to an output transducer of the system.

In an embodiment, the hearing assistance system is configured to determine one or more processed endocochlear potentials from the 'raw' endocochlear potentials (picked up by one or more sensing electrodes, possibly relative to a reference potential) according to a predefined algorithm, e.g. a statistical algorithm or model (e.g. an averaging algorithm, e.g. a moving average). In an embodiment, the one or more processed endocochlear potentials (or voltage differences) is/are determined from spatially distributed 'raw' values of the endocochlear potentials (e.g. picked up at various different locations along the cochlear partition, e.g. by a multi-electrode array sensing electrode). In an embodiment, the one or more processed endocochlear potentials is/are determined from 'raw' values of the endocochlear potentials (or voltage differences) taken at different points in time (e.g. picked up by the same electrode). In an embodiment, the one or more processed endocochlear potentials (or voltage differences) is/are determined from values of the endocochlear potentials taken at the same or different points in time and picked up at various different locations along the cochlear partition.

In an embodiment, the hearing assistance system is configured to estimate a present hearing threshold of the user from the 'raw' or 'processed' endocochlear potentials measured at a given time or over a given time range (e.g. an average value over time, e.g. a moving average) and/or at spatially different locations along the cochlear partition.

Such estimation may be based on empirical data. In an embodiment, the hearing aid system comprises (or has access to) a database comprising corresponding values of hearing thresholds and endocochlear potentials for various age groups (e.g. for children, middle aged, or elderly people) and gender (male, female) at one or more frequencies or frequency ranges. In an embodiment, the database comprises historic corresponding values of the user's hearing thresholds and endocochlear potentials. Such data may be used by the hearing assistance system to improve the estimate of the user's present hearing threshold from measured present endocochlear potentials.

In an embodiment, the signal processor is adapted to modify presently used processing parameters of the hearing assistance system (e.g. level compression parameters, frequency compression parameters, frequency dependent gains, etc.), based on estimated present hearing thresholds of the user (such estimation being e.g. influenced by present values of endocochlear potentials). Alternatively, such parameters may be determined in advance and stored in a database containing corresponding values of endocochlear potentials for the user in question (and thus be used as a look-up table using present values of endocochlear potentials as input and processing parameters as output).

In an embodiment, such modification of the processing parameters is performed according to a predefined scheme, e.g. with a predefined update frequency, and/or if said currently estimated hearing thresholds deviate with a predefined amount from the presently used hearing thresholds. In an embodiment, a hearing threshold difference measure is defined and used to determine said predefined amount. In an embodiment, the hearing threshold difference measure comprises a sum ($\Delta HT_{cur}$) of the differences between the currently estimated hearing thresholds (CEHT(f)) and the presently used hearing thresholds (PUHT(f)), where f is frequency. In an embodiment, the hearing thresholds are estimated at a number NHT of predefined frequencies, $f_1$, $f_2$, $f_{NHT}$. In an embodiment, NHT is smaller than or equal to 12, e.g. in the range from 1 to 10. In an embodiment, the predefined frequencies comprise one or more of (such as a majority or all of) 250 Hz, 500 Hz, 1 kHz, 1.5 kHz, 2 kHz, 3 kHz, 4 kHz and 6 kHz. In an embodiment, the adaptation of processing parameters based on measurements of present endocochlear potentials is performed at the request of a user, e.g. via a user interface of the hearing assistance system (e.g. a remote control, e.g. implemented as an APP of a SmartPhone).

In an embodiment, the hearing assistance system comprises a user interface. In an embodiment the hearing assistance system is configured to sense (measure) endocochlear potentials initiated by a user or a hearing care professional (e.g. via the user interface). In an embodiment, the hearing assistance system is configured to present data related to the measured (and/or stored) endocochlear potentials via said user interface (including alarm indications or information related thereto).

In an embodiment, the implanted part comprises a multi electrode array e.g. in the form of a carrier comprising a multitude of electrodes adapted for being located in the cochlea in proximity of an auditory nerve of the user, e.g. fully or partially in scala tympani. The carrier is preferably flexible to allow a proper positioning of the electrodes in cochlea to achieve that the electrodes can be inserted in cochlea. Preferably, the individual electrodes are spatially distributed along the length of the carrier to provide a corresponding spatial distribution along the cochlear nerve when the carrier is inserted in cochlea of a person in a way allowing the electric stimulation signal to be applied to the auditory nerve and possibly allowing a response signal to said stimulation (potentially) comprising a response from the nerve to be measured (i.e. each electrode being individually accessible for sensing its potential).

In an embodiment, the multi-electrode array is in communication with the sensing unit.

In an embodiment, at least one of the electrodes of the multi electrode array are configured to be used as a reference electrode for the endocochlear potentials. In such case, the at least one electrode being used as a reference electrode is preferably located in cochlea in fluid contact with perilymph, e.g. in scala tympani or in scala vestibuli.

In an embodiment, at least one of the electrodes of the multi-electrode array is configured to be used as an EP-electrode. In such case, the multi-electrode array is preferably adapted for being positioned along the cochlear partition (including the cochlear nerve), preferably to be located in the scala media of the user's cochlea and configured to pick up endocochlear potentials at its location (or their respective locations).

In an embodiment, the hearing assistance device is a portable device.

In an embodiment, the implanted part is fully or partially powered from the endocochlear potentials. In an embodiment, the sensing unit and/or a possible transmission unit is powered by the endocochlear potentials.

In an embodiment, the hearing assistance device comprises a local energy source, e.g. a battery, e.g. a rechargeable battery. In an embodiment, energy for the hearing assistance device is supplied in part by a battery and in part by endocochlear potentials.

In an embodiment, the hearing assistance system is adapted to determine at least an estimate of the real or absolute time elapsed between two time instances where endocochlear potentials (and/or estimates of hearing thresholds, etc.) are measured (or determined) and possibly stored. In an embodiment, the hearing assistance system is adapted to receive a signal representative of the present time from another device, e.g. from a cell phone, or a charging unit, or from a transmitter of a radio time signal (e.g. DCF77 or MSF). In an embodiment, the hearing assistance system comprises a real time clock circuit and a battery ensuring a constant functioning of the clock.

In an embodiment, the hearing assistance system is adapted to provide a frequency dependent gain to compensate for a hearing loss of a user.

In an embodiment, the hearing assistance system comprises an output transducer for converting an electric signal to a stimulus perceived by the user as an acoustic signal. In an embodiment, the output transducer comprises a number of electrodes of a cochlear implant or a vibrator of a bone conducting hearing device. In an embodiment, the output transducer comprises a receiver (loudspeaker) for providing the stimulus as an acoustic signal to the user. In a particular embodiment, the hearing assistance system comprises an output transducer comprising a number of electrodes for electrical stimulation of the cochlear nerve as well as an output transducer in the form of a loudspeaker for acoustic stimulation of the ear through (normal) air conduction.

In an embodiment, the hearing assistance system (e.g. the input unit) comprises an input transducer for converting an input sound to an electric input signal.

In an embodiment, the hearing assistance system (e.g. the input unit) comprises an antenna and transceiver circuitry for wirelessly receiving a direct electric input signal from another device, e.g. a communication device or another hearing assistance device.

In an embodiment, the hearing assistance system comprises a forward or signal path between an input transducer (microphone system and/or direct electric input (e.g. a wireless receiver)) and an output transducer. In an embodiment, the signal processing unit is located in the forward path. In an embodiment, the signal processing unit is adapted to provide a frequency dependent gain according to a user's particular needs. In an embodiment, the hearing assistance system comprises an analysis path comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain. In an embodiment, some or all signal processing of the forward path is conducted in the time domain, whereas some or all signal processing of the analysis path in the frequency domain.

In an embodiment, the hearing assistance devices comprise an analogue-to-digital (AD) converter to digitize an analogue input with a predefined sampling rate, e.g. 20 kHz. In an embodiment, the hearing assistance devices comprise a digital-to-analogue (DA) converter to convert a digital signal to an analogue output signal, e.g. for being presented to a user via an output transducer.

In an embodiment, the hearing assistance device, e.g. the input unit, comprise(s) a TF-conversion unit for providing a time-frequency representation of an input signal. In an embodiment, the frequency range considered by the hearing assistance system from a minimum frequency $f_{min}$ to a maximum frequency $f_{max}$ comprises a part of the typical human audible frequency range from 20 Hz to 20 kHz, e.g. a part of the range from 20 Hz to 12 kHz.

In an embodiment, the hearing assistance system further comprises other relevant functionality for the application in question, e.g. feedback cancellation, level compression, frequency compression, noise reduction, etc.

In an embodiment, the hearing assistance system comprises a hearing assistance device, e.g. a hearing aid, e.g. a hearing instrument, e.g. a hearing instrument adapted for being located at the ear, or fully or partially in the ear canal, or fully or partially implanted in the head, of a user, or e.g. a headset, an earphone, an ear protection device or a combination thereof.

In an embodiment, the hearing assistance system comprises an auxiliary device. In an embodiment, the system is adapted to establish a communication link between the hearing assistance device and the auxiliary device to provide that information (e.g. control and status signals (e.g. endocochlear potentials or signals derived therefrom), possibly audio signals) can be exchanged or forwarded from one to the other.

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing assistance device. In an embodiment, the auxiliary device is or comprises a remote control for controlling functionality and operation of the hearing assistance device(s). In an embodiment, the auxiliary device is or comprises a cellular telephone, e.g. a SmartPhone. In an embodiment, the function of a remote control is implemented in a SmartPhone, the SmartPhone possibly running an APP allowing to control the functionality of the audio processing device via the SmartPhone (the hearing assistance device(s) comprising an appropriate wireless interface to the SmartPhone, e.g. based on Bluetooth or some other standardized or proprietary scheme). In an embodiment, a user interface is implemented in the auxiliary device. In an embodiment, a measurement of endocochlear potentials can be initiated via the user interface.

In the present context, a SmartPhone, may comprise

- a (A) cellular telephone comprising a microphone, a speaker, and a (wireless) interface to the public switched telephone network (PSTN) COMBINED with
- a (B) personal computer comprising a processor, a memory, an operative system (OS), a user interface (e.g. a keyboard and display, e.g. integrated in a touch sensitive display) and a wireless data interface (including a Web-browser), allowing a user to download and execute application programs (APPs) implementing specific functional features (e.g. displaying information retrieved from the Internet, remotely controlling another device, combining information from various sensors of the smartphone (e.g. camera, scanner, GPS, microphone, etc.) and/or external sensors to provide special features, etc.).

In an embodiment, the auxiliary device is another hearing assistance device.

In an embodiment, the listening system comprises two hearing assistance devices adapted to implement a binaural listening system, e.g. a binaural hearing aid system.

Use:

In an aspect, use of a hearing assistance device as described above, in the 'detailed description of embodiments' and in the claims, is moreover provided.

A Method:

In an aspect, a method of operating a hearing assistance system for processing an input signal representative of sound according to a user's needs, the hearing assistance system comprising an input unit for receiving said input signal and providing an electric input signal, a signal processing unit for processing said electric input signal according to a set of processing parameters and providing a processed output signal, the signal processing unit having one or more control inputs for influencing said processing parameters is furthermore provided by the present application. The method comprises sensing endocochlear potentials (EP) at one or more positions along the length of the cochlear partition;

receiving said endocochlear potentials or signals derived therefrom, and transforming the received signals into signals appropriately conditioned for use as control inputs to the signal processing unit; and processing the electric input signal in dependence of said control inputs.

It is intended that some or all of the structural features of the system described above, in the 'detailed description of embodiments' or in the claims can be combined with embodiments of the method, when appropriately substituted by a corresponding process and vice versa. Embodiments of the method have the same advantages as the corresponding systems.

A Computer Readable Medium:

In an aspect, a tangible computer-readable medium storing a computer program comprising program code means for causing a data processing system to perform at least some (such as a majority or all) of the steps of the method described above, in the 'detailed description of embodiments' and in the claims, when said computer program is executed on the data processing system is furthermore provided by the present application. In addition to being stored on a tangible medium such as diskettes, CD-ROM-, DVD-, or hard disk media, or any other machine readable medium, and used when read directly from such tangible media, the computer program can also be transmitted via a transmission medium such as a wired or wireless link or a network, e.g. the Internet, and loaded into a data processing system for being executed at a location different from that of the tangible medium.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

Definitions:

In the present context, a 'hearing assistance device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing assistance device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing assistance device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing assistance device may comprise a single unit or several units communicating electronically with each other.

More generally, a hearing assistance device comprises an input transducer for receiving an acoustic signal from a user's surroundings and providing a corresponding input audio signal and/or a receiver for electronically (i.e. wired or wirelessly) receiving an input audio signal, a signal processing circuit for processing the input audio signal and an output means for providing an audible signal to the user in dependence on the processed audio signal. In some hearing assistance devices, an amplifier may constitute the signal processing circuit. In some hearing assistance devices, the output means may comprise an output transducer, such as e.g. a loudspeaker for providing an air-borne acoustic signal or a vibrator for providing a structure-borne or liquid-borne acoustic signal. In some hearing assistance devices, the output means may comprise one or more output electrodes for providing electric signals.

In some hearing assistance devices, the vibrator may be adapted to provide a structure-borne acoustic signal transcutaneously or percutaneously to the skull bone. In some hearing assistance devices, the vibrator may be implanted in the middle ear and/or in the inner ear. In some hearing assistance devices, the vibrator may be adapted to provide a structure-borne acoustic signal to a middle-ear bone and/or to the cochlea. In some hearing assistance devices, the vibrator may be adapted to provide a liquid-borne acoustic signal to the cochlear liquid, e.g. through the oval window. In some hearing assistance devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

A 'hearing assistance system' refers to a system comprising one or two hearing assistance devices, and a 'binaural listening system' refers to a system comprising one or two hearing assistance devices and being adapted to cooperatively provide audible signals to both of the user's ears. Listening systems or binaural listening systems may further comprise 'auxiliary devices', which communicate with the hearing assistance devices and affect and/or benefit from the function of the hearing assistance devices. Auxiliary devices may be e.g. remote controls, audio gateway devices, mobile phones, public-address systems, car audio systems or music players. Hearing assistance devices, listening systems or binaural listening systems may e.g. be used for compensating for a hearing-impaired person's loss of hearing capability, augmenting or protecting a normal-hearing person's hearing capability and/or conveying electronic audio signals to a person.

Further objects of the application are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which.

The figures are schematic and simplified for clarity, and they just show details which are essential to the understanding of the disclosure, while other details are left out.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The present disclosure proposes to use a measurement of the endocochlear potential at different points in time (and optionally at different locations along the cochlear nerve) to indicate an 'effective state' of cochlea (or a specific part thereof) at such points in time. By correlating such present 'effective state' with average hearing loss data (e.g. stored in or accessible to a hearing assistance system), processing parameters can be optimized using a (e.g. on-board) fitting algorithm.

FIG. 1 shows an embodiment of a hearing assistance system according to the present disclosure and various cross sections of cochlea illustrating location of EP- and reference electrodes.

Figure 1A:
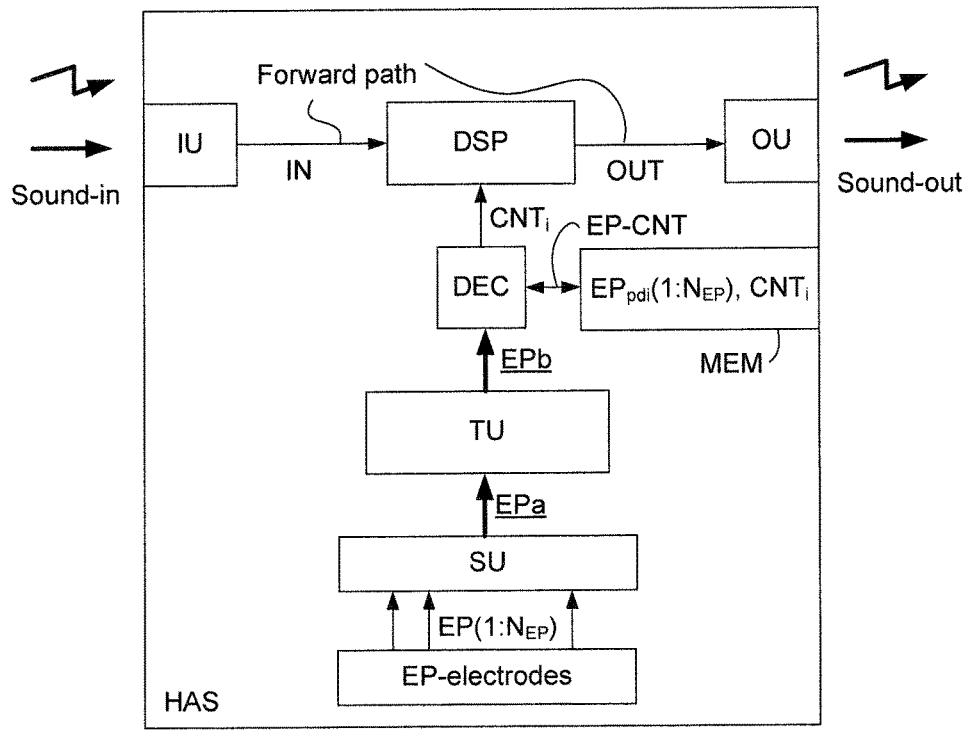
FIGS. 1A-1D show an embodiment of a hearing assistance system according to the present disclosure, FIG. 1A showing a block diagram of the system, FIG. 1B schematically showing a cross section of cochlea including a pickup or sensing electrode of endocochlear potentials, FIG. 1C and 1D schematically showing a perspective cross section of cochlea with respective embodiments of sensing electrodes, FIGS. 2A-2C schematically show various partitions of a hearing assistance system according to the present disclosure, in FIG. 2A a hearing assistance system in its most basic form comprising only an (self-contained) implanted part, in FIG. 2B a hearing assistance system comprising an implanted part and an external part with a wireless communication link between them, and in FIG. 2C a hearing assistance system as in FIG. 2B but where the external part comprises an antenna part for establishing the wireless link to the implanted part and a processing part for processing an audio signal, and where the antenna and processing parts are connected by a wired link (e.g. a cable), FIGS. 3A-3B schematically show a link between average (e.g. age dependent) hearing loss vs. frequency and endocochlear potentials for female (FIG. 3A) and male (FIG. 3B) users.

FIG. 1A shows a block diagram of a hearing assistance system (HAS) according to the present disclosure. The hearing assistance system comprises a hearing assistance device comprising a forward path (Forward path) from an input unit (IU), providing an electric input signal IN from a sound input (Sound-in), to an output unit (OU), providing an output signal (Sound-out) perceivable by a user as sound from an electric output signal OUT. The forward path comprises a signal processing unit (DSP) for processing (e.g. applying a frequency dependent gain to) the signal (IN) picked up or received by the input unit (IU, e.g. a microphone and/or a wireless receiver) and providing an enhanced signal (OUT) to the output unit (OU, e.g. an output transducer or a multi-electrode array or a wireless transceiver). The input and output units may e.g. comprise analogue-to-digital (AD) and digital-to-analogue (DA) converters, respectively, to allow digital processing of signals in the forward path (and possible elsewhere in the system, as appropriate). The input and output units may further comprise analysis and synthesis filterbanks, respectively, to allow processing of signals in the forward path (and possible elsewhere in the system, as appropriate) to be performed in the (time-)frequency domain. The signal processing unit (DSP) comprises one or more control inputs $CNT_i$ for influencing the processing parameters used by the signal processing unit, thereby allowing the processing of the electric input signal (IN) to be modified according to such control input(s) $CNT_i$. The hearing assistance system further comprises a number $N_{EP}$ of electrodes (termed EP-electrodes) adapted to be located (e.g. implanted or inserted) in the user's cochlea and adapted for picking up (measuring) an endocochlear potential (EP) at a corresponding number of positions along the length of the cochlear nerve (signals $EP(1:N_{EP})$). At least some of the electrodes (e.g. one, or several, such as all EP-electrode(s)) is (are) adapted for being located in scala media in contact with endolymph. In an embodiment, the hearing assistance device comprises a reference electrode providing a common potential for the endocochlear potentials. In an embodiment, the reference electrode is located outside the scala meida, e.g. in scala tympani or vestibuli, and in contact with perilymph. In an embodiment, the reference electrode is located outside cochlea. In an embodiment, the reference electrode is located externally (with respect to the head of the user; i.e. not implanted, but e.g. arranged to be in contact with the scalp of the user). The EP-electrodes (and optionally the reference electrode) are electrically connected to (or form part of) a sensing unit (SU) for capturing the endocochlear potentials of the EP-electrode(s) and forwarding the captured potentials (or signals derived therefrom) EPa to a transmission unit (TU). The transmission unit (TU), be it a wireless transceiver or a driver for a wired connection depending on the practical solution, forwards the resulting EP-signals EPb to a decoding unit (DEC). The decoding unit (DEC) is configured to receive the transmitted/forwarded endocochlear potentials or signals derived therefrom (resulting EP-signals EPb, e.g. voltage differences) from the sensing unit (SU) and to transform the received signals into signals appropriately conditioned for use as control inputs ($CNT_i$) to the signal processing unit (SPU). The sensing unit (SU) may comprise some sort of processing of the captured endocochlear potentials, e.g. generation of voltage differences, amplification, noise reduction, averaging, etc.). The signal processing unit (SPU) is configured to process the electric input signal (IN) in dependence of the control inputs ($CNT_i$) from the decoding unit (DEC). Hence, the signal processing unit is adapted to process (or to influence the processing of) a signal of the forward path in dependence of the current endocochlear potentials. In an embodiment, the hearing assistance system (HAS) comprises a memory (MEM) comprising a database of corresponding data of predetermined endocochlear potentials (or appropriately processed signals derived from the potentials, e.g. voltage differences relative to a common reference potential) $EP_{pdi}(1:N_{EP})$ and control signals ($CNT_i$) reflecting a state of the cochlear nerve (e.g. a particular hearing threshold or an estimated hearing loss). When the decoding unit (DEC) receives a current set of resulting EP-signals EPb from the transmission unit, it acquires from the memory unit (MEM) the control signals ($CNT_i$) corresponding to the set of predetermined endocochlear potentials $EP_{pdi}(1:N_{EP})$, which (most closely) resemble the current set of resulting EP-signals EPb (e.g. based on interpolation), cf. signal EP-CNT between the decoder (DEC) and memory (MEM) units. Alternatively, an algorithm for determining the appropriate control signals ($CNT_i$) from the current set of resulting EP-signals EPb may be stored in the memory unit and used for to determine the control signals ($CNT_i$) indicative of a current state of cochlea.

The decoding unit may e.g. be located in an external part of the hearing assistance system (in which case the transmission unit (TU) comprises a wireless transceiver, e.g. a capacitive or an inductive transceiver.

The EP-electrode(s) and the reference electrode may be implanted and located in cochlea for an extended time (months, years, permanently). For an initial investigation relating to the characteristics (e.g. level) of endocochlear response of a user (e.g. measurements performed during fitting), the EP-electrode(s) and/or the reference electrode(s) may be temporarily inserted in cochlea (e.g. through the oval window).

The hearing assistance system of FIG. 1A may be partitioned in a number of ways according to its use. It may e.g. be embodied in an implanted part and an external part. Various examples of such partition are described in connection with FIG. 2.

Figure 1B:
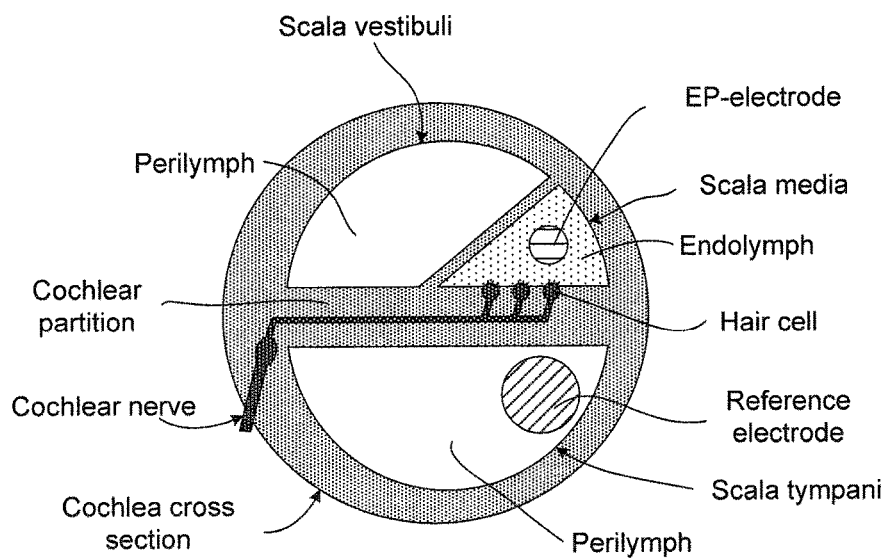

FIG. 1B schematically shows a (transversal) cross section of cochlea (Cochlea cross section in FIG. 1B) including a pickup or sensing electrode of endocochlear potentials (EP-electrode in FIG. 1B) and a reference electrode (Reference electrode in FIG. 1B). The sensing electrode (EP-electrode) is located in scala media (Scala media) in fluid contact with endolymph (Endolymph). The reference electrode is in the transversal cross-sectional view of cochlea of FIG. 1B located at an inner wall in the right side of scala tympani (Scala tympani). It may, however, be located other places in the scala tympani or in scala vestibuli (Scala vestibuli, in both cases, preferably immersed in perilymph (Perilymph). The cochlear partition (Cochlear partition) hosting (a part of) the cochlear nerve (Cochlear nerve) and separating the Scala media and Scala vestibuli from the Scala tympani, is schematically indicated in FIG. 1B. The cochlear nerve comprises hair cells (Hair cell) reaching into Scala media.

Figure 1C:
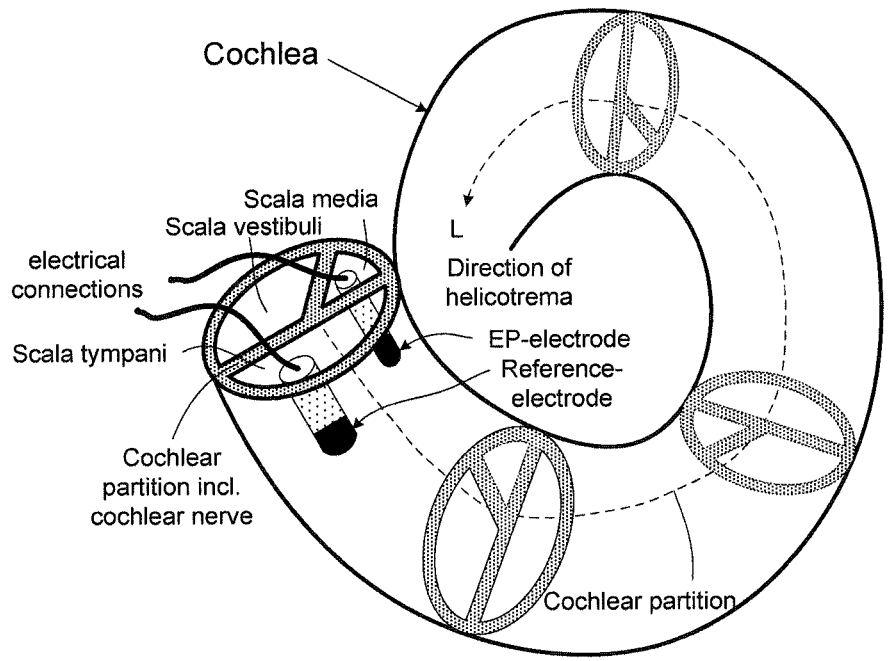
Figure 1D:
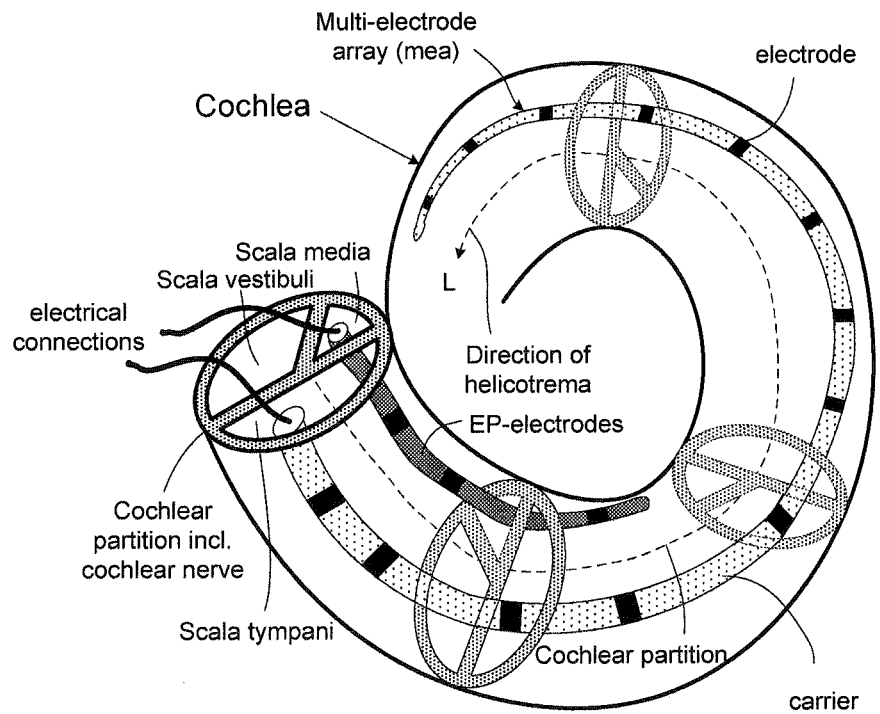

FIGS. 1C and 1D schematically shows respective perspective cross-sectional views of cochlea (Cochlea) with respective exemplary embodiments of sensing electrode(s) of endocochlear potentials (EP-electrode) and the reference electrode(s) (Reference electrode). The schematic cross sections illustrate a longitudinal (helical) extension of cochlea by dashed arrow denoted L (length) and indicating a Direction of helicotrema, where Scala tympani and Scala vestibuli meet. In the embodiment of FIG. 1C, the EP-electrode is a single electrode located at the entrance of scala media (near the oval window, at the opposite end of cochlea compared to helicotrema). Likewise, the reference electrode is a single electrode located at the entrance of scala tympani, e.g. accessed through the oval window. The two electrodes are connected to electrical connections (electrical connections, e.g. conducting wires) connectable to the sensing unit (SU).

The embodiment of FIG. 1D comprises a number of electrodes for capturing endocochlear potentials (EP-electrodes in FIG. 1D) in the form of a multi electrode array located in scala media in a longitudinal direction starting from the oval window. Likewise, the reference electrode is shown as a multi-electrode array, which may be a multi-electrode array (Multi-electrode array (mea) in FIG. 1D) of a cochlear implant type hearing assistance device (for stimulating the cochlear nerve at different locations along its extension in cochlea (and optionally for capturing corresponding nerve responses)). Both multi electrode arrays comprise a carrier (carrier) comprising a number of electrodes (electrode) distributed along the length (cf. dashed arrow denoted L) of the carrier. Each electrode (electrode) is configured to be electrically connected to the sensing unit (SU, cf. FIG. 1A) as indicated by the bold lines denoted electrical connections in FIG. 1D. In this embodiment, an appropriate reference electrode along the length of cochlea may be selected, or a number of electrodes (e.g. all) may be electrically connected to have a distributed reference electrode. The multi-electrode array (EP-electrodes) constituting the EP-electrodes may in an embodiment be distributed along the full length of the scala media (or as shown over a part of its length). In an embodiment, endocochlear potentials $EP(x_i)$ (i=1, 2, ..., $N_L$), where $N_L$ is the number of locations (electrodes) along the cochlear nerve, may be captured along the length of cochlear nerve by individually reading the potential of each of the electrodes of the multi-electrode array (either sequentially in time or in parallel (simultaneously)). The acquisition of the endocochlear potentials $EP(x_i)$ and/or the configuration of the reference electrode(s) may be controlled from the sensing unit (SU), e.g. via a user interface (cf. FIG. 6) or fixed during fitting or manufacture of the system.

FIG. 2 shows various partitions of a hearing assistance system according to the present disclosure.

Figure 2A:
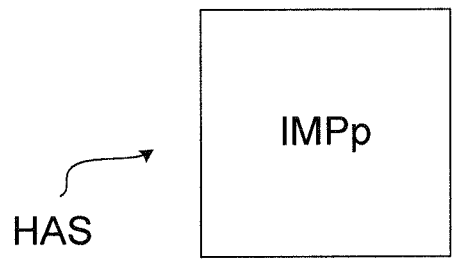

FIG. 2A shows a hearing assistance system (HAS) comprising only a, preferably self-contained, implanted part ($IMP_p$). In an embodiment, the implanted part is battery driven. In an embodiment, the implanted part comprises an input unit (IU in FIG. 1A), e.g. an input transducer, e.g. a microphone (or microphone system) and/or a wireless receiver, and an output unit (OU in FIG. 1A), e.g. comprising a loudspeaker, a vibrator or one or more electrodes for stimulating the auditory nerve. Additionally, the implanted part ($IMP_p$) comprises the other basic functional parts of the hearing assistance system as illustrated in FIG. 1A, including the sensing unit for sensing endocochlear potentials of the endolymph of cochlea. In the embodiment of FIG. 2A, the transmission unit (TU in FIG. 1A) is configured to relay the (possibly amplified) endocochlear potentials received from the sensing unit (SU) to the decoding unit (DEC in FIG. 1A), i.e. no (wireless) transmission is necessary.

Figure 2B:
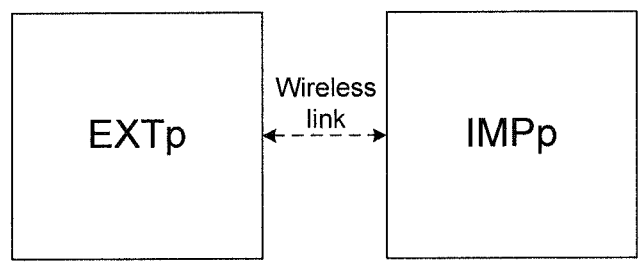

FIG. 2B shows a hearing assistance system (HAS) comprising an implanted part ($IMP_p$) and an external part ($EXT_p$) with a wireless (e.g. inductive) communication link (Wireless link) between them allowing a transfer of the endocochlear potentials (or signals derived therefrom) from the implanted part ($IMP_p$) to the external part ($EXT_p$). The external part ($EXT_p$) may e.g. comprise the forward path of the hearing assistance system including the input unit (IU in FIG. 1A), the signal processing unit (DSP in FIG. 1A) for enhancing a received electric input signal IN, and the output unit (OU in FIG. 1A). The external part ($EXT_p$) may further comprise the decoding unit (DEC) for determining processing parameters corresponding to the presently measured endocochlear potentials, and for applying such processing parameters to the signal processing unit (DSP) of the forward path. Alternatively, the output unit (OU) may form part of the implanted part ($IMP_p$) and have the form of a multi-array electrode located in cochlea for stimulating a cochlear nerve of the user. Alternatively, the output unit (OU) may be distributed between the implanted and external parts, e.g. comprising a multi-array electrode for stimulating a cochlear nerve of the user in the implanted part, and comprising an electromechanical transducer (vibrator) for bone conduction and/or a loudspeaker for air conduction as an external part.

Figure 2C:
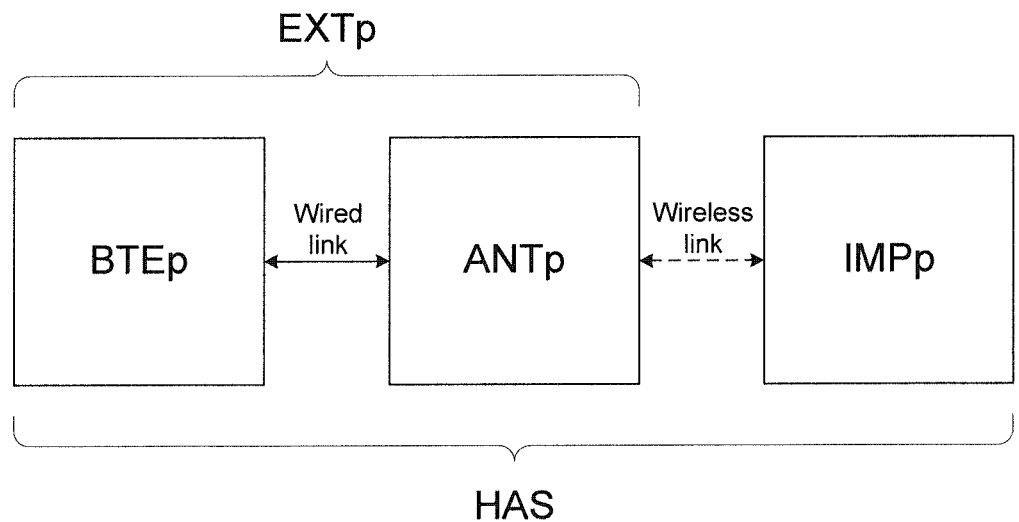

FIG. 2C shows a hearing assistance system (HAS) as in FIG. 2B but where the external part ($EXT_p$) comprises an antenna part ($ANT_p$) for establishing the wireless link to the implanted part ($IMP_p$) and a processing part ($BTE_p$) for processing an audio signal, and where the antenna and processing parts are connected by a wired link (Wired link, e.g. a cable). The processing part ($BTE_p$) may e.g. comprise the same functional parts as described in connection with FIG. 2B (except for the (inductive) antenna and possible modulation/demodulation circuitry).

Other partitions may be relevant depending on the practical application, including wired or wireless connections/links according to need.

Figure 3A:
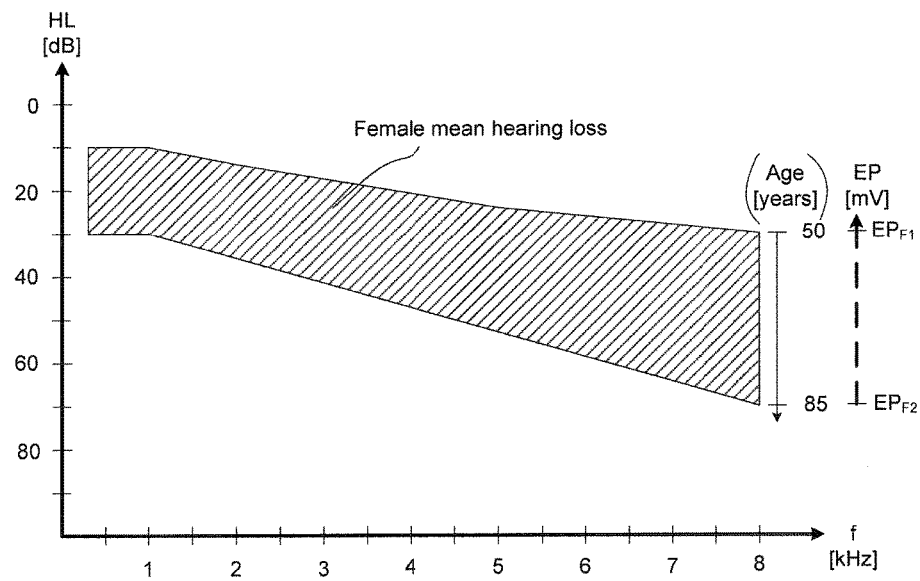
Figure 3B:
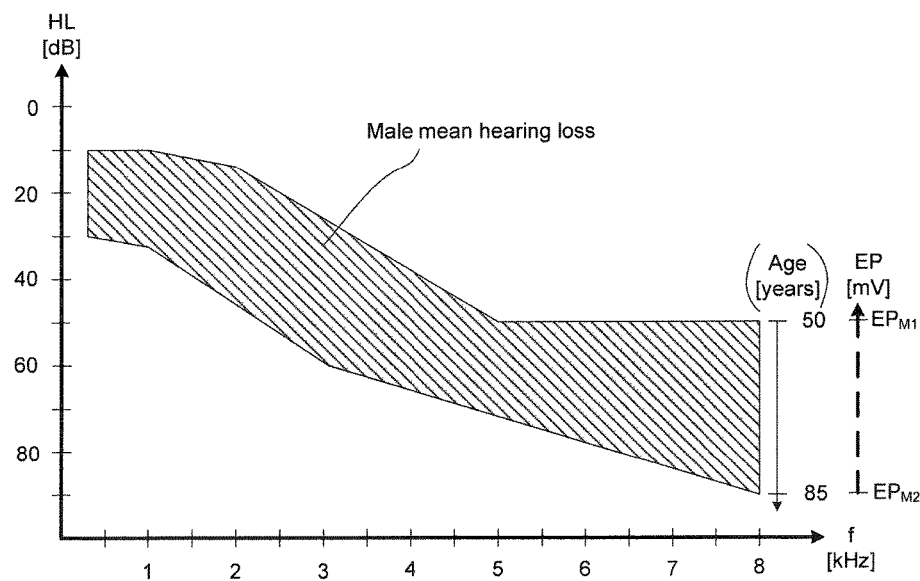

FIG. 3 schematically shows a link between average (age dependent) hearing loss (HL [dB]) vs. frequency (f [kHz]) and endocochlear potentials (EP [mV]) for female (FIG. 3A) and male (FIG. 3B) users. Such data are well known in the art and e.g. presented in [Schmiedt; 2010] (FIG. 2.4, page 18 ff.). Ignoring the (typical) age relationship (as indicated by the parenthesis around Age [years]), the graphs relate hearing loss (HL(f)) to endocochlear potentials (EP) for female and male persons, respectively. Such data (and other similar data from the literature) may be used to generate corresponding values of hearing loss (e.g. hearing thresholds vs frequency or at a specific frequency) and endochochlear potentials (relative to a common reference, e.g. ground). For each gender (or for both genders at one time) an algorithm may, alternatively, be extracted. Specific values of the endocochlear potential $EP_j$ may be associated with a specific hearing loss curve $HL_j(f)$, j=1, 2, ..., $N_{EPdata}$, where $N_{EPdata}$ is the number of different sets of EP-values and associated hearing loss curves, which have been stored (e.g. in a database accessible to the hearing aid system). Again an algorithm providing continuous values of HL(f) from EP-values may be extracted from empirical data, and/or from measurements on the individual user (e.g. during fitting, e.g. using acoustic doses and/or medical treatment to modify endocochlear potentials in a controlled way to generate such personalized relationship between hearing threshold and endocochlear potentials).

Figure 4:
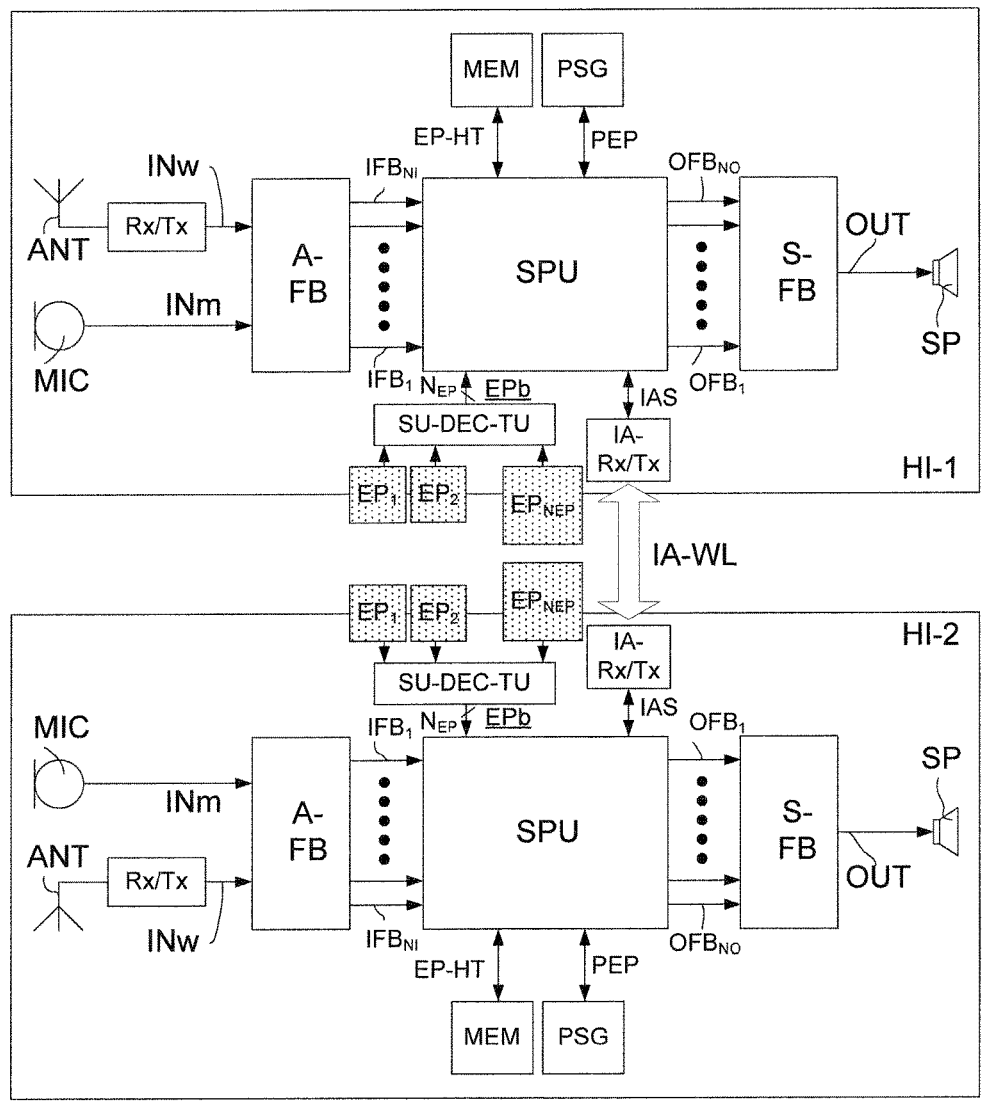
FIG. 4 shows an embodiment of a binaural hearing assistance system comprising first and second hearing instruments in communication with each other, each comprising a sensing unit for endocochlear potentials.

FIG. 4 shows an embodiment of a binaural hearing assistance system comprising first and second hearing instruments (HI-1, HI-2) adapted for being located at or in left and right ears of a user and comprising a part to be fully or partially implanted in a user's head. The hearing instruments are adapted for exchanging information between them via a wireless communication link, e.g. a specific inter-aural (IA) wireless link (IA-WL) or, alternatively, a wired connection. The two hearing instruments HI-1, HI-2 are adapted to allow the exchange of endocochlear potentials (e.g. signals EPb) picked up by an instrument at a particular ear to the instrument at the other ear. To establish the inter-aural link, each hearing instrument comprises antenna and transceiver circuitry (here indicated by block IA-Rx/Tx). Each hearing instrument HI-1 and HI-2 is an embodiment of a hearing assistance system as described in the present application, e.g. as described in connection with FIG. 1. In the embodiment of FIG. 4, the sensing (SU), transmission (TU) and decoding (DEC) units are indicated (e.g. integrated) in one unit, denoted SU-DEC-TU. Further, the input (IU) and output (OU) units of FIG. 1 are in each of the hearing instruments (HI-1, HI-2) of FIG. 4 embodied in a microphone (MIC) (providing electric inputs signal INm) and a loudspeaker (SP) (converting output signal OUT to a sound signal for presentation to the left and right ears of a user), respectively. The memory unit (MEM) comprising a database of corresponding data of predetermined endocochlear potentials and control signals reflecting a state of the cochlear nerve is in the embodiment of FIG. 4 shown to be in electrical contact with the control and signal processing unit (SPU). The control signals (denoted EP-HT in FIG. 4) are accessible to the combined unit SU-DEC-TU via the control and signal processing unit (SPU), which comprises the function of the signal processing unit (DSP) of the embodiment of FIG. 1A. In the binaural hearing aid system of FIG. 4, a signal IAS generated by a control part of the control and processing unit (SPU) of one of the hearing instruments (e.g. HI-1) and comprising endocochlear potentials (or data derived therefrom, e.g. an 'effective state' of the cochlea of the user) is transmitted to the other hearing instrument (e.g. HI-2) and/or vice versa. The control signals from the local and the opposite device are e.g. used together to influence a decision or a parameter setting in the local device. The control signals may e.g. comprise other information that enhances system quality to a user, e.g. to improve signal processing. The control signals IAS may e.g. (in addition to the endocochlear potentials) comprise directional information or information relating to a classification of the current acoustic environment of the user wearing the hearing instruments, etc. In an embodiment, the binaural hearing assistance system further comprises an audio gateway device (e.g. a cellular telephone, e.g. a SmartPhone) for receiving a number of audio signals and for transmitting at least one of the received audio signals to the hearing assistance systems (e.g. via antenna and transceiver circuitry (ANT, Rx/Tx), cf. received audio signal INw of hearing instruments HI-1, HI-2), e.g. transmitted according to a communication standard, e.g. Bluetooth, e.g. Bluetooth Low Energy.

The hearing assistance systems (HI-1, HI-2) of FIG. 4 comprise an analysis filter bank (A-FB) (generating band split input signals $IFB_1:FB_{NI}$ (from one or both of the input audio signals INm and INw), where NI is the number of input bands) and a synthesis filter bank (S-FB) (generating output signal OUT from band split output signals $OFB_1:OFB_{NO}$, where NO is the number of output bands), respectively, to provide signal processing in the (time-) frequency domain.

The hearing instruments (HI-1, HI-2) of FIG. 4 further comprise an analysis probe signal generator (PSG) configured to generate a specific probe signal PEP adapted to excite the Endolymph at specific points in time (or activated via a user interface (e.g. a remote control, e.g. a SmartPhone)) before the endocochlear potentials are measured. In an embodiment, the analysis probe signal generator (PSG) is configured to excite particular frequencies according to a predefined scheme, and/or to generate a predefined acoustic dose (over a predefined time). In an embodiment, corresponding values of endocochlear potentials and hearing loss are determined (measured) in connection with the activation of the analysis probe signal generator (PSG), e.g. in a fitting session to create a user specific database for storage in the hearing assistance system (e.g. in MEM-units of one or both hearing instruments).

Figure 5:
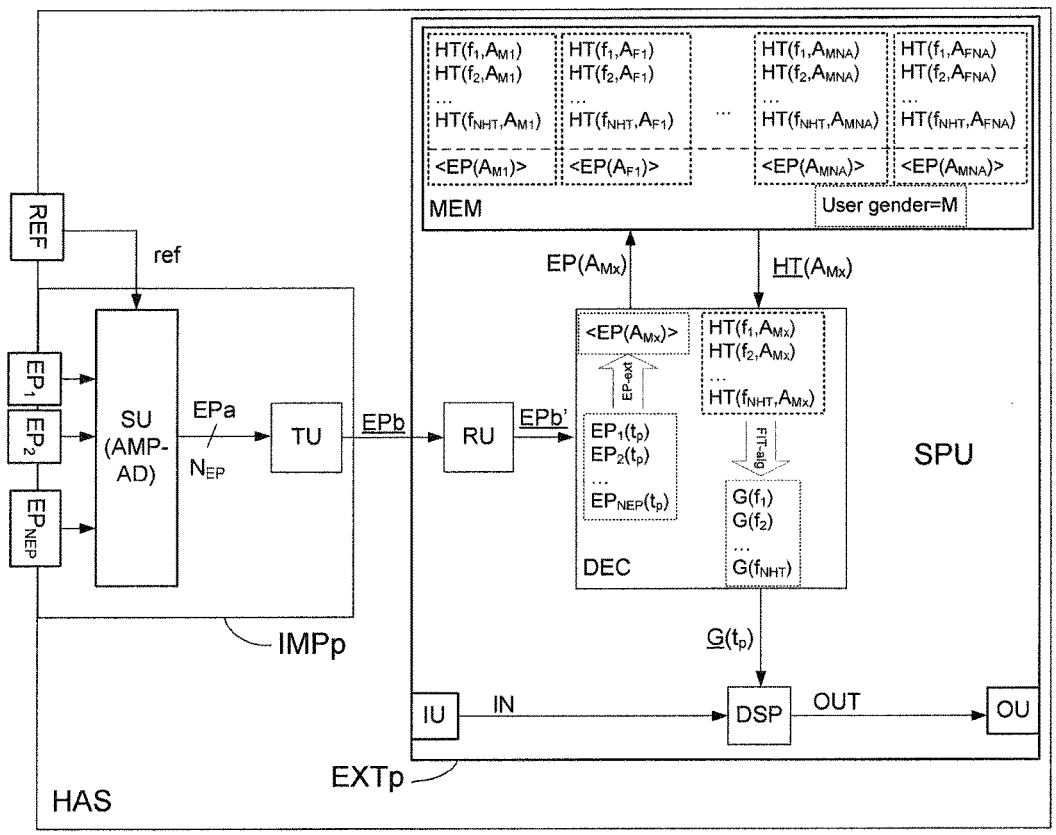
FIG. 5 shows an embodiment of a hearing assistance system according to the present disclosure, wherein a determination of processing parameters influenced by a measurement of endocochlear potentials is illustrated.

FIG. 5 shows an embodiment of a hearing assistance system (HAS) according to the present disclosure, wherein a determination of (frequency (f) dependent) processing parameters $(G(f_1), G(f_2), \ldots, G(f_{NHT}))$ of a signal processing unit (DSP) of the forward path of the hearing assistance system (HAS) adapted to a measurement of endocochlear potentials (values $EP_1(t_p), EP_2(t_p), \ldots, EP_{NEP}(t_p)$) measured at time $t_p$) is illustrated. The hearing assistance system of FIG. 5 comprises the same functional elements as described in connection with FIG. 1A. The hearing assistance system (HAS) comprises an implanted part ($IMP_p$) and an external part ($EXT_p$). The implanted part ($IMP_p$) comprises the endocochlear electrodes ($EP_1, EP_2, \ldots, EP_{NEP}$) and a reference electrode (REF) connected to the sensing unit (SU (AMP-AD), the sensing unit comprising appropriate amplification (AMP) and analogue to digital conversion (AD) functionality). The implanted part ($IMP_p$) further comprises the transmission unit (TU) connected to the sensing unit SU (via signals EPa). The sensing unit (SU (AMP-AD) provides one or more captured endocochlear potentials (or signals derived therefrom, e.g. voltage differences taken relative to reference voltage ref provided by the reference electrode (REF)) EPa to the transmission unit (TU). The transmission unit (TU) forwards these resulting potentials EPb to the external part ($EXT_p$) via an appropriate communication interface, e.g. a wireless interface, e.g. an inductive communication interface based on inductive coupling between inductor coils located in the implanted and external parts (e.g. in respective transmission and reception units), respectively, when in close proximity to each other (e.g. only separated by skin/tissue of the user). The external part ($EXT_p$) comprises a reception unit (RU) configured to receive the resulting potentials EPb (e.g. comprising an inductor coil and appropriate demodulation circuitry) and to provide corresponding signals EPb' (e.g comprising signals $EP_1(t_p), EP_2(t_p), EP_{NEP}(t_p)$ measured at time $t_p$) to the decoding unit (DEC). The decoding unit is in communication with memory MEM and signal processing unit (DSP). The memory unit (MEM) comprises a database of corresponding values of predetermined endocochlear potentials (or signals derived therefrom) and hearning loss curves $HT(f_i)$, i=1, 2, . . . , $N_{HT}$) for male (M) and female (F) persons. With a given value (e.g. an average value <EP $(A_{Mx})$>) $EP(A_{Mx})$ of the currently (at time $=t_p$) measured endocochlear potentials ($EP_1(t_p), EP_2(t_p), EP_{NEP}(t_p)$) for a male person, a corresponding hearing loss curve $HT(fi, A_{Mx})$ (hearing thresholds versus frequency at a number $N_{HT}$ of frequencies) is read from the database and imported to the sensing unit (SU). Using an algorithm for determining appropriate frequency dependent gains ($G(f_1), G(f_2), G(f_{NHT})$) (a fitting rationale), signal processing parameters (here denoted gains G) $G(t_p)$ of the signal processing unit (DSP) are updated corresponding to the current ($t=t_p$) endocochlear potentials. Thereby, a signal IN of the forward path provided by input unit (IN) is processed according to the current state of cochlea and an enhanced signal OUT is provided to the output unit (OU). It should be mentioned that other effects than the endococlear potentials (e.g. a current feedback situation) may contribute to the 'final current signal processing parameters', but such contributions are neglected here for simplicity.

Figure 6:
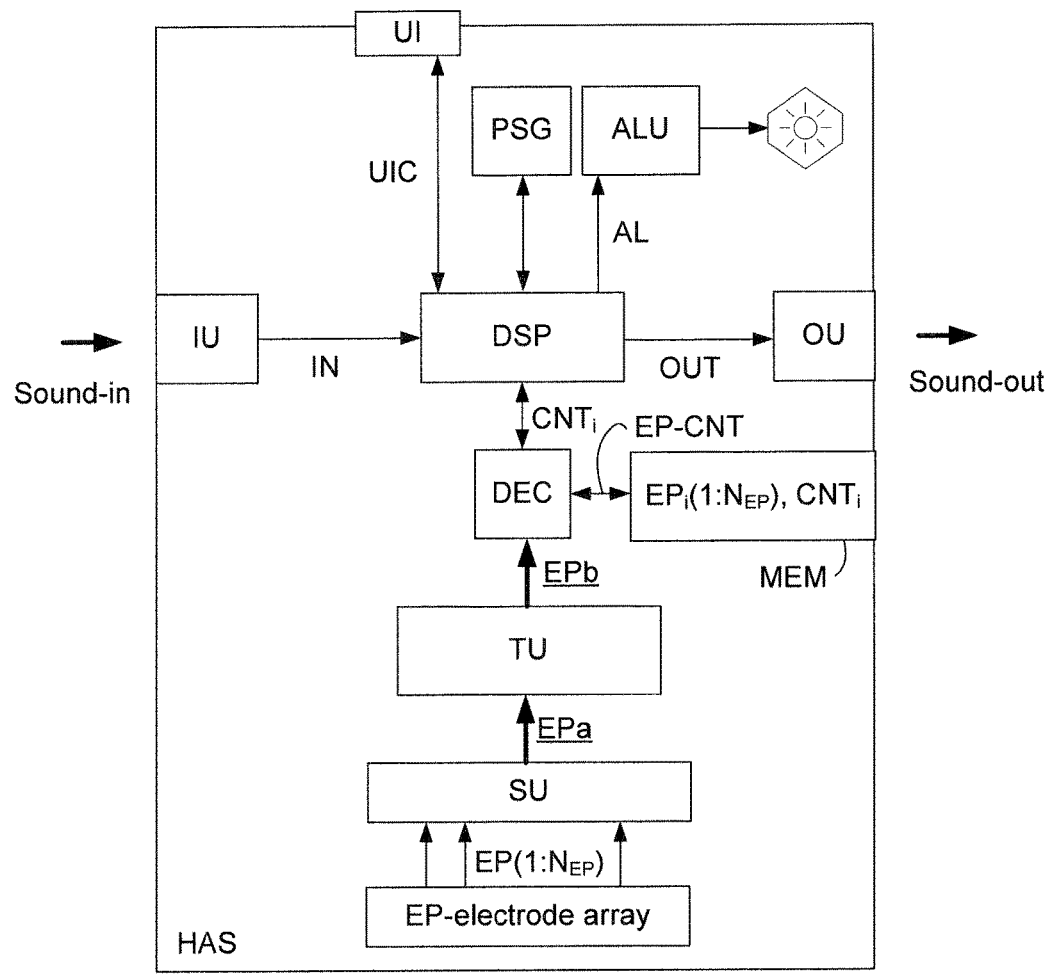
FIG. 6 shows an embodiment of a hearing assistance system according to the present disclosure comprising a user interface for influencing the measurement of endocochlear potentials and/or for the update of processing parameters based on endocochlear potentials and/or for the presentation of information related to the same.

FIG. 6 shows an embodiment of a hearing assistance system (HAS) according to the present disclosure comprising a user interface (UI) for influencing the update of processing parameters based on endocochlear potentials and/or for the presentation of information related to the same. The embodiment of FIG. 6 is equivalent to the embodiment of FIG. 1A, apart from the additional user interface (UI), and the alarm indication unit (ALU). The user interface may e.g. be used to initiate an adaptation of processing parameters based on measurements of present endocochlear potentials. The user interface (UI) may e.g. be implemented as a button or another activation element on the hearing assistance system (HAS). Alternatively, or additionally, the user interface (UI) may be implemented in a remote control unit, e.g. implemented in a SmartPhone. The alarm unit (ALU), e.g. comprising a visual and/or an acoustic and/or a vibrational indicator, may be configured to issue an alarm indication, when one or more specific criteria regarding the endocochlear potentials are fulfilled. In an embodiment, the user interface (UI) and/or the alarm unit (ALU) are integrated in an APP of a SmartPhone.

FIG. 7 shows FIGS. 7A-7D show four different configurations (FIGS. 7A, 7B, 7C and 7D) of a hearing assistance system according to the present disclosure.

Figure 7A:
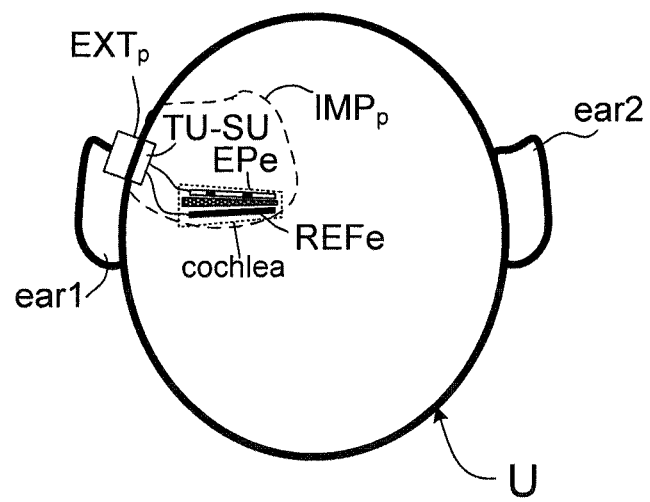
FIGS. 7A-7D show four different configurations (FIG. 7A, 7B, 7C and 7D) of a hearing assistance system according to the present disclosure.

FIG. 7A illustrates a hearing assistance system comprising a bone anchored type hearing assistance device and electrodes (EPe) for capturing endocochlear potentials (and a reference electrode (RFEe)) according to the present disclosure. The output unit (OU in FIG. 1A) of the hearing assistance system located in external part ($EXT_p$), mounted at a first ear (ear1) of the user (U), is a (possibly bone anchored) vibrator of a bone conduction type hearing assistance device for converting electrical stimuli to a bone vibration configured to be perceived by the user as an auditory signal (sound). The implanted part ($IMP_p$) is indicated by the dashed enclosure in the user's (U) head and comprises the EP- and reference electrodes (EPe and REFe, respectively) implanted into the cochlea (cochlea) of the user and the sensing and transmission units (TU-SU).

Figure 7B:
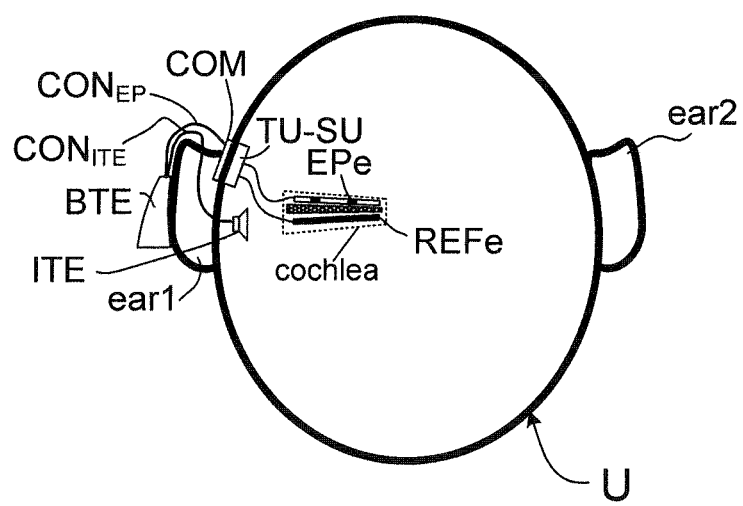

FIG. 7B illustrates a hearing assistance system comprising an air conduction type hearing assistance device and electrodes for capturing endocochlear potentials according to the present disclosure. The output unit (OU in FIG. 1A) of the hearing assistance system is located in external part ($EXT_p$), mounted at a first ear (ear1) of the user (U). The output unit comprises a loudspeaker (ITE) located in the ear canal of the user U and intended to stimulate the user's ear drum and middle ear with mechanical vibration. The loudspeaker unit is—via electrical conductors $CON_{ITE}$—connected to a BTE-part (BTE), which is located behind the ear (ear1) of the user (U). The implanted part ($IMP_p$) comprises the EP- and reference electrodes (EPe and REFe, respectively) implanted into the cochlea (cochlea) of the user and the sensing and transmission units (TU-SU). The endocochlear potentials (or signals derived therefrom) are communicated to the external part (here to the BTE-part) via the transmission unit (TU) of the implanted part, external communication unit (COM), the TU- and COM-units implementing a wireless link, and electrical connection $CON_{EP}$, e.g. a cable, between the communication unit (COM) and the BTE-unit.

Figure 7C:
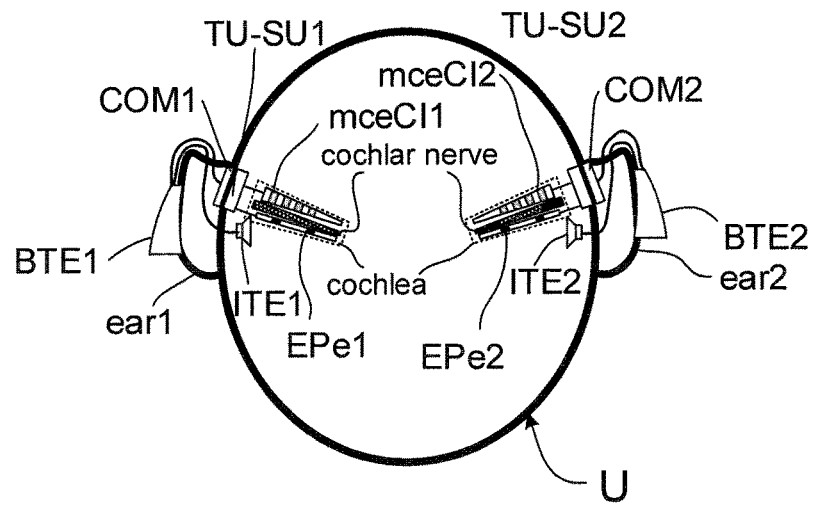
Figure 7D:
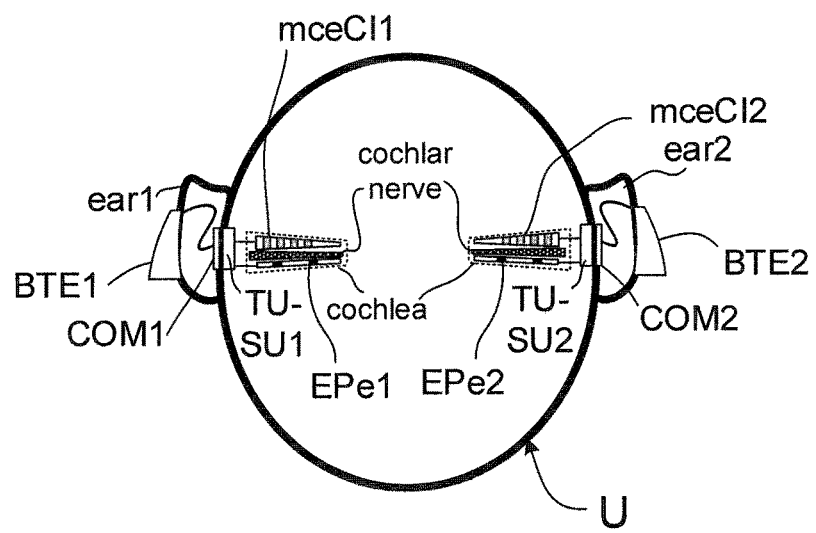

FIGS. 7C and 7D show two embodiments of bilateral hearing assistance systems.

The bilateral hearing assistance systems of FIGS. 7C and 7D comprise first and second hearing assistance devices of the cochlear implant type, each device comprising an implanted part comprising a multi-channel electrode array mceCl1, mceCl2, respectively, implanted into cochlea (cochlea) near a respective cochlear nerve (cochlear nerve). The implanted parts further comprise respective electrodes (EPe1, EPe2, respectively) for picking up endocochlear potentials, and sensing and transmission units (TU-SU1, TU-SU2, respectively) as described in connection with FIG. 1A and FIG. 7A, 7B. Each hearing assistance device further comprises one or more external parts, here a part (BTE1, BTE2, respectively) adapted to be located behind an ear (ear1, ear2, respectively) of the user U and a communication part (COM1, COM2, respectively) adapted to be located on the head at an ear, at a position allowing a (e.g. wireless) communication link to the implanted part to be established (including allowing the transfer of stimuli (or coded stimuli) to the multi-channel electrode array, possibly allowing the transfer of energy to the implanted part and possibly allowing the reception in the respective BTE parts of data from the implanted part (e.g. nerve responses (eCAPs), endocochlear potentials (EP), etc.). The respective BTE and COM parts are here shown to be electrically connected by a cable (indicated by a bold, curved connection in FIGS. 7C and 7D).

FIG. 7C illustrates a hearing assistance system comprising first and second hybrid hearing assistance devices of the cochlear implant and air conduction type together with respective electrodes for capturing endocochlear potentials according to the present disclosure. The first and second hearing assistance devices are each implemented as hybrid solutions comprising a cochlear implant multi-electrode array (mceCl1, mceCl2, respectively) for electrically stimulating the cochlear nerve as well as an electro-acoustical transducer (e.g. a loudspeaker, ITE1, ITE2, respectively) for acoustically stimulating the ear drum and middle ear (air conduction) to utilize residual hearing provided by intact hair cells (e.g. at relatively low frequencies), if any.

FIG. 7D illustrates a hearing assistance system comprising first and second hearing assistance devices of the cochlear implant type together with respective electrodes (EPe1 and EPe2, respectively) for capturing endocochlear potentials according to the present disclosure. In this system the information gathered from the measurement of endocochlear potentials in the media scala of the respective cochlea may contribute to dynamic evaluation of the state of the user's auditory system, in particular the current condition of cochlea. Again, such information about the current state of the cochlea may be used to influence the stimulation of the electrodes of the multi-electrode arrays (mceCl1 and mceCl2, respectively)

Other combinations of hearing assistance devices with the endocochlear electrode concepts of the present disclosure may be envisioned.

Although the description so far is concerned with monitoring EP and using the measured values to control a processing algorithm in a hearing assistance device, the present concepts might also allow for the EP-powered transmission of other cochlear status signals, as yet unknown.

Further possibilities include the telemetric use of received cochlear status signals (maybe combined with parameters of the acoustic input signals) to trigger a message to the user, e.g. "your current noise exposure is causing metabolic stress to your ears and endangering your hearing—you are advised to find a less noisy place", or "Cochlear status indicates that your Meniere's symptoms may soon be aggravated" (could appear as a screen message on a pocketed smartphone, i.e. the device does not have to be in use). The message could instead be directed to a caregiver or physician etc.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims and equivalents thereof.

REFERENCES

[Mercier et al, 2012] Patrick P Mercier, Andrew C Lysaght, Saurav Bandyopadhyay, Anantha P Chandrakasan, Konstantina M Stankovic, Energy extraction from the biologic battery in the inner ear, nature biotechnology letters, published online 8 Nov. 2012, 5 pages, doi: 10.1038/nbt.2394.

[Schmiedt; 2010] Richard A. Schmiedt, The Physiology of Cochlear Presbycusis, Chapter 2, pp. 9-38, in S. Gordon-Salant et al. (eds.), The Aging Auditory System, Springer Handbook of Auditory Research 34, DOI 10.1007/978-1-4419-0993-0_2, © Springer Science+Business Media, LLC, 2010.

US2012300964A1 (SAMSUNG) 29 Nov. 2012

EP2200347A2 (OTICON) 23 Jun. 2010

The invention claimed is:

1. A hearing assistance system for processing an input signal representative of sound according to a user's needs, the hearing assistance system comprising:
    an input unit for receiving said input signal and providing an electric input signal;
    a signal processing unit for processing said electric input signal according to a set of processing parameters and providing a processed output signal, the signal processing unit having one or more control inputs for influencing said processing parameters;
    an implanted part adapted for being at least partially implanted in a user's head, wherein the implanted part comprises
        a sensing unit capable of measuring an endocochlear potential (EP), generated by metabolic processes in the cochlea of the user, at one or more positions along a length of the cochlear partition, and
        an EP-electrode configured to be located in scala media in fluid contact with endolymph and to pick up said endocochlear potential at a position along the length of the cochlear partition; and
    a decoder, configured to receive said endocochlear potentials or signals derived therefrom and to transform the received signals into signals appropriately conditioned for use as control inputs to the signal processing unit, and
    wherein the signal processing unit is configured to process the electric input signal in dependence of said control inputs from said decoder.

2. A hearing assistance system according to claim 1, wherein the implanted part comprises a transmission unit for transmitting said endocochlear potential (EP) or a signal based thereon to an external reception unit.

3. A hearing assistance system according to claim 1, wherein the implanted part is configured to measure said endocochlear potential (EP) at different points in time.

4. A hearing assistance system according to claim 1, wherein the hearing assistance system comprises an alarm unit configured to issue an alarm indication to the user according to a predefined criterion.

5. A hearing assistance system according to claim 1, wherein the implanted part comprises number of EP-electrodes for picking up said endocochlear potentials (EP) at said number of positions along the length of the cochlear partition.

6. A hearing assistance system according to claim 1, wherein the implanted part comprises a reference electrode.

7. A hearing assistance system according to claim 5 configured to measure or determine resulting voltage differences $\Delta V_{EP}(x_i)$ for endocochlear potentials (EP($x_i$), i=1, 2, . . ., $N_L$) measured at a number $N_L$ of locations along a cochlear nerve.

8. A hearing assistance system according to claim 1 configured to evaluate a current state or condition of a cochlea or cochlear nerve based on the measured endocochlear potentials.

9. A hearing assistance system according to claim 8 configured to base said evaluation on statistical measures derived from said measured endocochlear potentials over time and/or location.

10. A hearing assistance system according to claim 1 comprises a database wherein data linking endocochlear potentials to estimated hearing loss are stored.

11. A hearing assistance system according to claim 1, wherein the implanted part comprises a multi electrode array in the form of a carrier comprising a multitude of electrodes adapted for being located in the cochlea in proximity of an auditory nerve of the user.

12. A hearing assistance system according to claim 1, wherein the implanted part is fully or partially powered from the endocochlear potentials.

13. A hearing assistance system according to claim 1 comprising a hearing assistance device in the form of a hearing aid adapted for being located at the ear, or fully or partially in the ear canal, or fully or partially implanted in the head, of a user, a headset, an earphone, an ear protection device or a combination thereof.

14. A hearing assistance system according to claim 13 comprising an auxiliary device wherein the system is adapted to establish a communication link between the hearing assistance device and the auxiliary device to provide that information can be exchanged or forwarded from one to the other.

15. A hearing assistance system according to claim 14 wherein the auxiliary device is or comprises a cellular telephone.

16. A hearing assistance system according to claim 15 wherein a function of a remote control is implemented in a SmartPhone, the SmartPhone running an APP allowing to control the functionality of the hearing assistance device via the SmartPhone and being configured to allow initiation of a measurement of endocochlear potentials.

17. A method of operating a hearing assistance system for processing an input signal representative of sound according to a user's needs, the hearing assistance system comprising an input unit for receiving said input signal and providing an electric input signal, a signal processing unit for processing said electric input signal according to a set of processing parameters and providing a processed output signal, the signal processing unit having one or more control inputs for influencing said processing parameters, the method comprising:
    sensing endocochlear potentials (EP), generated by metabolic processes in the cochlea of the user, at one or more positions along a length of the cochlear partition using an implanted part at least partially implanted in a user's head, the implanted part including an EP-electrode located in scala media in fluid contact with endolymph;

receiving said endocochlear potentials or signals derived therefrom, and transforming the received signals into signals appropriately conditioned for use as control inputs to the signal processing unit;

processing the electric input signal in dependence of said control inputs.

18. Use of a hearing assistance system as claimed in claim 1.

19. A hearing assistance system comprising:

a sensing unit capable of sensing an endocochlear potential, generated by metabolic processes in the cochlea of the user, at one or more positions along a length of the cochlear partition using at least one EP-electrode located in scala media in fluid contact with endolymph, and configured to broadcast this data, and a hearing assistance device comprising
- a receiver configured to receive the data from the sensing unit,
- a decoder, configured to transform the received signals into signals appropriately conditioned for use as control variables in the hearing assistance device,
- a signal processing unit configured to perform calculations integrating cochlear status signals into an overall calculation scheme of the hearing assistance device, such that manipulations of input signals of the hearing assistance device may be modified in dependence thereof.

* * * * *